United States Patent

Brenneisen

[11] Patent Number: 5,727,042
[45] Date of Patent: Mar. 10, 1998

[54] METHOD AND DEVICE FOR THE CORRECT POSITIONING OF A TARGET FOR RADIATION TREATMENT

[76] Inventor: Werner Brenneisen, Raschplatz 5, 30161 Hannover, Germany

[21] Appl. No.: 689,991

[22] Filed: Aug. 16, 1996

[30] Foreign Application Priority Data

Aug. 16, 1995 [DE] Germany ................ 195 30 013.0

[51] Int. Cl.⁶ .................................................. A61N 5/10
[52] U.S. Cl. ................................. 378/65; 378/208
[58] Field of Search ......................... 378/205, 65, 64, 378/901; 128/303 B; 606/130

[56] References Cited

U.S. PATENT DOCUMENTS

| | | | |
|---|---|---|---|
| 4,618,978 | 10/1986 | Cosman | 606/130 |
| 5,107,839 | 4/1992 | Houdek et al. | 128/653.1 |
| 5,329,567 | 7/1994 | Ikebe | 378/20 |

FOREIGN PATENT DOCUMENTS

WO 94/28973  12/1994  WIPO.

*Primary Examiner*—Don Wong
*Attorney, Agent, or Firm*—Collard & Roe, P.C.

[57] ABSTRACT

A method and device for correctly positioning a target within the target range of a radiation treatment apparatus by adjusting the target range to coincide with coordinates that have been assigned to the target. The adjustment is determined by selecting a reference point having a known spacial relation to the target range, and selecting a reference surface having a known spacial relation to the target. The spacing between the reference point and the reference surface is then measured and adjusted so that the target range and the target are in the same plane, having identical coordinates along one axis. The other coordinates of the target are then located on the reference surface, so that the target range can be exactly aligned with the target.

21 Claims, 4 Drawing Sheets

METHOD AND DEVICE FOR THE CORRECT POSITIONING OF A TARGET FOR RADIATION TREATMENT

BACKGROUND OF THE INVENTION

1. Field of the Invention

The invention relates to a method and apparatus to correctly position a target to be irradiated, particularly a tumor, in the isocenter of a radiation treatment apparatus, such as a linear accelerator. The isocenter forms a target range, whereby coordinates that have been previously assigned to the target are located by adjusting the target range to the coordinates.

2. The Prior Art

Methods for correctly positioning radiation targets are described in U.S. Pat. No. 5,329,567, U.S. Pat. No. 5,107,839 and PCT Application WO 94/28973, and are commonly used in stereotaxy. Positioning devices of the type described in these references are sold on the market with different designs.

The following procedure is used in the art for a stereotaxy:

A patient having been diagnosed with disease such as a brain tumor which is to be irradiated by rays of a linear accelerator, has a stereotaxy frame or framework-like sight unit placed around the frontal region of his or her head. The sight unit is immovably fixed on the head of the patient such as by screws which penetrate into the skull bone of the patient.

The sight unit usually has three plates arranged in the form of box walls, namely, one plate in front of the forehead or face of the patient, and two plates arranged at right angles relative to the front plate on the two temple sides of the patient. A reference system with Cartesian coordinates is pre-established on the plates. The plates usually also have markings of the coordinates, which can be seen in X-ray pictures. In this way, such markings permit corresponding coordinate measurements on X-ray pictures as well.

The skull of the patient, and therefore the brain tumor contained in the skull, is included in the reference system. Therefore, in the reference system, clear Cartesian coordinates, namely X-, Y- and Z-coordinates, can be assigned to the location of the brain tumor. Normally, the Y-axis extends from the back side of the skull in the direction of the frontal side, and the X-axis extends from the right temple side in the direction of the left temple side of the patient. The Z-axis extends from the chin side of the skull to the vault of the cranium, or in the reverse direction, because the direction or the sign of Z-coordinate is irrelevant.

So as to exactly measure and fix the respective coordinates of the brain tumor, and to fix such coordinates within the stereotaxy frame, a computertomography of the skull of the patient is carried out. During the computertomography, the stereotaxy frame is immovably arranged on the patient's skull. With such computertomography, sectional views of the skull of the patient are prepared by X-ray pictures, usually in sectional skull planes. Thus, image planes following each other with small spacings in the Z-direction of the system of coordinates are prepared. Based on the markings on the plates, which are arranged opposing each other on the temple sides next to the skull of the patient as components of the stereotaxy frame, it is possible to exactly determine and measure the Z-spacings of the individual X-ray pictures. Therefore, it is possible to exactly determine the Z-coordinate of each individual picture. Each X-ray picture itself shows the X-Y-plane of the coordinate system preset by the stereotaxy frame. On the X-ray pictures, in which the brain tumor can be seen, it is thus possible to exactly measure the tumor's Y- and X-coordinates. Based on said measured Y- and X-coordinates, and on the basis of the Z-coordinate, which is determined from the measured X-ray picture, the position of the brain tumor can be exactly fixed in the stereotaxy frame.

If a brain tumor, whose coordinates have been exactly fixed in the reference system, is to be irradiated with a radiation treatment apparatus such as a linear accelerator, the brain tumor must be exactly positioned in the field of rays. This field should be made as small as possible for radiation safety reasons. Therefore, the field of radiation must be positioned as exactly and rapidly and simply as possible.

For radiation treatment, the stereotaxy frame is affixed on the patient's head and is brought into the radiation treatment apparatus. This apparatus consists of a treatment table, whose table top is displaceable by a motor in two directions in the plane of the table top and also up and down, and the actual irradiation device. This irradiation device directs a radiation beam onto the head of the patient resting on the treatment table, and it can be pivoted around a horizontal axis extending parallel with the longitudinal axis of the patient, so that an irradiation of the skull could take place around the head of the patient. In the irradiation, the irradiation device is in fact swiveled back and forth around the axis of pivot, swinging by a certain angle.

Furthermore, the treatment table is pivotable around a vertical axis, which is disposed on the face side of the treatment table on which the head of the patient is resting.

The sight unit on the patient's head can be affixed in a highly-defined position and orientation on the face side so that following the fixing of this position, the sight unit is immobile in relation to the treatment table. Upon fixing this sight unit in position, the head of the patient is immovably locked in the sight unit.

The axis of radiation of the radiation treatment apparatus intersects the vertical axis of pivot of the treatment table and with the horizontal axis of pivot of the irradiation device in a common point, called the isocenter. The isocenter is the target range of the radiation treatment apparatus, i.e. the location where the radiation beam is direction at all times. The isocenter, therefore, must be aligned with the localized tumor, i.e., during the treatment, the tumor must be located exactly in the isocenter of the irradiation apparatus. Since the beam emitted by the irradiation apparatus has a relatively small diameter, in the order of magnitude of only a few millimeters, the beam must be positioned exactly and correctly. In particular, the tumor must be exactly in the isocenter or target range. The irradiation device is pivoted during treatment around the horizontal so the tumor can be irradiated by the device from different directions across a certain angular range.

The following procedure is used for positioning the tumor in the isocenter: The respective X, Y and Z coordinates are first marked on the three plates of the sight unit. For example, the point of intersection of the Y- and Z-coordinates of the brain tumor is marked on the plates opposing each other on the temple sides, whereas the point of intersection of the X- and Z-coordinates is marked on the plate on the frontal side.

An optical laser beam unit is normally installed where the radiation treatment apparatus is disposed. This laser beam unit reproduces the course of the axes of swivel and the axis of radiation of the irradiation device with three laser rays. The laser enables the isocenter or target range to be optically visible in the point of intersection of the three laser rays in the darkened room. The table top is displaceable in its plane in orthogonal direction, which each coincide with the Z-axis and the X-axis of the system of coordinates, and also may perform a lifting motion parallel to the Y-axis of the system of coordinates. By displacing this table top, the patient, who is locked in the sight unit, can be moved in a defined way in the directions of the coordinate axes. Therefore, it is possible, by moving the table, to position the brain tumor in the isocenter or target range of the radiation treatment apparatus. Exact positioning is achieved when the respective laser beams exactly contact the corresponding markings on the three plates of the sight unit. Such markings may be made in the form of crosses marked by pencil, or by target prisms displaceable on a digital measuring device.

By aiming at the markings on the temple sides of the two plates of the sight unit, it is possible to determine whether the respective axes of the coordinates of the sight unit and the radiation treatment apparatus extend parallel with each other.

The conventional positioning method described above, and the positioning device required for this method, are relatively complicated. In particular, a laser beam emitter, which itself has to be exactly positioned, is required. The laser beam emitter's aiming accuracy also has to be checked prior to each treatment because of known third properties. Moreover, the three markings on the three plates of the sight unit have to be adjusted independently of one another and have to be targeted in the positioning process.

SUMMARY OF THE INVENTION

It is therefore an object of the present invention to overcome the drawbacks of the prior art and to provide a method and device to simplify the positioning process.

The present invention reduces the measurement of one of the coordinates to a very simple spacial measurement. In the present invention, a reference point and a reference surface are used as aids. The reference point has a known spacial relation to the target range of the radiation treatment apparatus, and the reference surface has a known spacial relation to the target on the patient. The coordinate of the target range is thus defined with respect to the reference point. The coordinate of the target is defined with respect to the reference surface. The measurement of the spacing between the reference point and the reference surface consequently results in an adjustment of the spacing between the coordinates of the target range and the target. The other coordinates of the target can then be found on the reference surface in a very simple way, keeping the target range in sync with the target. Usually, two additional coordinates will be used, in which the reference surface is a plane. However, other coordinate systems such as a polar coordinate system may be used. In a polar coordinate system, the reference surface would be a spherical surface.

A preferred embodiment of the invention uses a Cartesian system of coordinates and uses a plane as the reference surface. This method places the direction of radiation of the radiation treatment apparatus parallel with a coordinate axis of the reference system. A reference plane extending parallel with the two other coordinate axes is selected as the reference surface. The spacing between a selected reference point and the target range is a known factor and is measured parallel to the axis of radiation. Using this known factor, the spacing between the reference point and the selected reference plane is adjusted so that the spacing between the reference point and the target range is equal to the sum of the spacing between the coordinate of the reference plane and the target, plus the spacing between the coordinate of the reference plane and the reference point where the coordinate axis extends parallel to the axis of radiation. The other two coordinates of the target range are then adjusted in the reference plane in accordance with the coordinates of the target.

Therefore, the method of the present invention replaces a triple marking and a location of said three markings as used in the prior art by a simple spacing measurement and location of a single marking.

Therefore, the present invention can be carried out in a substantially simpler, more exact and more rapid way.

The measurements and adjustments made in accordance with the present invention ensure that the target is located in the target range, and preferably in the isocenter.

The method of the present invention can be carried out in the following way. The stereotaxy sight unit is fixedly mounted on the patient's head. This unit presets a reference system in which the coordinates of the target, e.g. the brain tumor, are determined. Therefore, the reference system can be viewed as the patient's own reference system. A reference plane is oriented parallel with the X-Z-plane of the reference system. The reference plane thus has a defined Y-coordinate ($Y_B$). For the sake of simplicity, the reference plane is selected in the site where the front-side plate of the stereotaxy sight unit is located, so that the front-side plate represents the selected reference plane.

Since the stereotaxy sight unit is fixed on the treatment table of the radiation treatment apparatus and also on the patient's head, the reference system preset by the sight unit is also an apparatus-integrated reference system, whose position within the treatment apparatus is known and unchangeable. However, the actual position of the reference system within the radiation treatment apparatus is irrelevant.

With the method according to the invention, it is necessary only to ensure that the axis of radiation of the radiation treatment apparatus is positioned parallel to the Y-axis of the reference system. The direction of radiation changes along this axis during the treatment once the alignment of the target range and target has been carried out. It would also be possible to carry out the method of the present invention without such alignment of the axis of radiation parallel with the Y-axis or another coordinate axis of the reference system. This would make the adjustment trigonometrically more complicated, but not impossible.

A reference point is fixed within the range of the radiation treatment apparatus. This reference point is preferably fixed on the axis of radiation itself, and more preferably within the range of the orifice where the beam exits from the irradiation head of the radiation treatment apparatus, such as within the outlet opening of a collimator system on the irradiation head. The reference point can also be fixed in another site as well. It is important that the spacing between the reference point and the isocenter or another fixed target range is known. This spacing is preferably parallel with the Y-axis of the system coordinates. Viewed from this reference point, it is thus known how far from the reference point the isocenter or the target range is removed. The spacing of the target from the reference plane, usually the front plate of the stereotaxy sight unit, is also known. The isocenter or the target range will be located on the same plane with the target if the spacing between the reference point and the reference plane, plus the spacing between the reference plane and the target, has the same length as the known spacing between the reference point and the isocenter or target range.

As soon as the respective spacing between the reference point and the reference plane has been adjusted, and the target range and the target are thus disposed in the same plane, namely in a plane parallel to the selected reference plane, the X- and Z-coordinates can be found by adjusting the point of intersection of the axis of radiation with the reference plane to the corresponding X- and Z-coordinates.

It is not important that the X-axis and the Z-axis are aligned in a certain way with the radiation treatment apparatus, because the X- and Z-coordinates are found directly on the reference plane, and may be calculated in any desired way. The X- and Z-coordinates may be established through suitable adjustments of the top of the treatment table. The vertical adjustment can be made by changing the height of the top of the treatment table.

With the method according to the invention, no additional references planes extending perpendicular to the selected reference plane are required. In particular, plates are not required on the temple sides of the patient's head when using a suitably designed stereotaxy sight unit. A plate is preferably affixed only to the frontal side. Thus, only one coordinate marking must be made. Furthermore, the method of the present invention makes it possible to eliminate the complicated and costly laser optics system, which itself requires adjustment.

In the method according to the invention, the spacing between the reference point and the reference plane is preferably measured mechanically, such as with a ruler. For this purpose, the reference plane is preferably formed by a plate, and a measuring rod is driven from the reference point up to the plate against a stop. Thus that with an axially displaceable measuring rod and suitable scaling, it is possible to measure the spacing in a very simple way.

Preferably, such a measuring rod is designed as an indicator which, with its free end, points at the reference plane or reference plate. The tip of the indicator can then be used for finding the other two coordinates on the plate or in the reference plane by driving it until it points at the desired marking. Such a marking could be made, for example, by a cross mark with a pencil. It would also be conceivable to use a preset marking whose location can be changed, such as a small depression into which an indicator could lock or immerse, triggering an electric signal. This procedure could also be carried out by making the indicator tip a component of a digitizer and having the reference surface function as a digitalizing tableau.

A preferred site for arranging such a measuring rod would be the beam exit bore of the radiation treatment apparatus. In this way, the measuring rod could be inserted with an exact fit. However, the spacing could also be measured electronically and/or optically.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
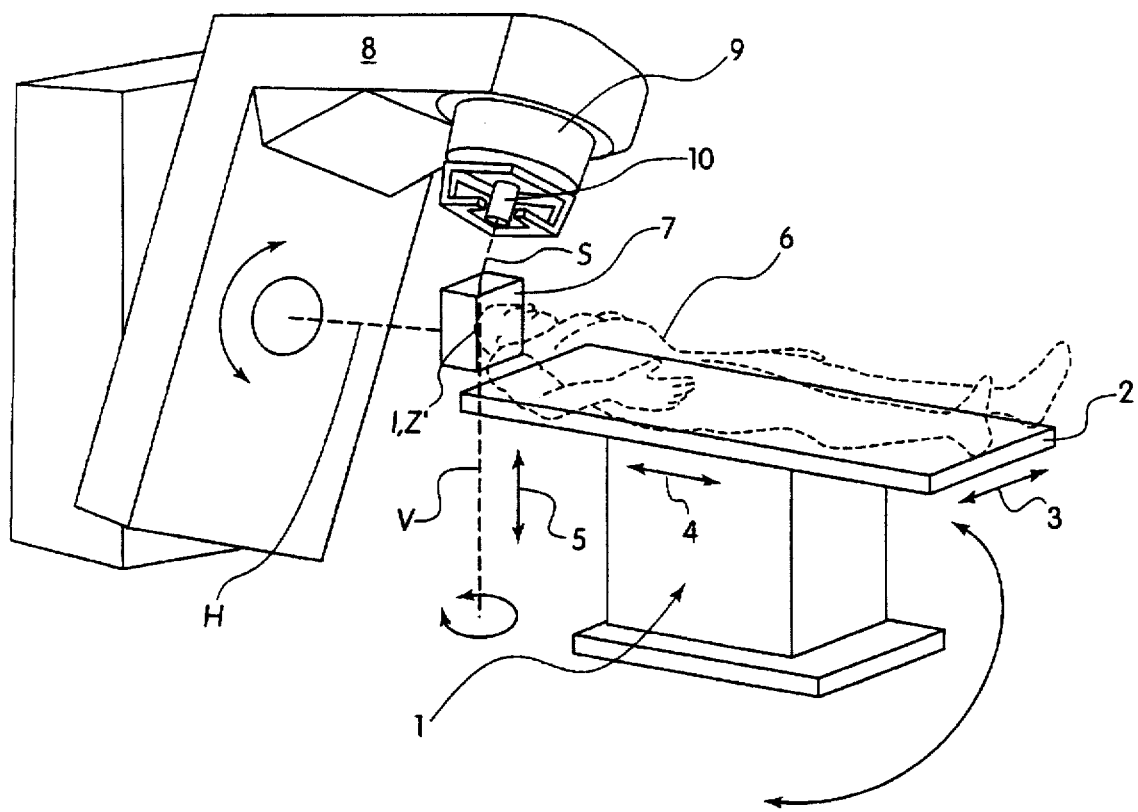
FIG. 1 is a schematic perspective view of a standard radiation treatment apparatus.

Referring now in detail to the drawings and, in particular, FIG. 1, which is a schematic, perspective view of a known radiation treatment apparatus, this apparatus comprises a treatment table 1, whose table top 2 can be changed in its position in three orthogonal directions according to double arrows 3 to 5. A patient 6, who is indicated by the dashed lines, can be placed laying down on treatment table 2.

A stereotaxy sight unit 7 is arranged and fixed on the head end of movable table top 3, said unit being designed as a frame- or box-like structure. This stereotaxy sight unit is immovably attached to head or skull 6, so that the head of patient 6 is immovably locked in stereotaxy sight unit 7, and consequently maintains a fixed position with respect to treatment table 1.

In this embodiment, the target to be treated with radiation, for example a brain tumor, is located within the head of patient 6.

The radiation treatment apparatus comprises the actual irradiation device 8 with an irradiation head 9, from which a beam 6 can exit through a radiation collimator 10 along an axis of radiation. A frame-like structure is arranged around the radiation collimator 10 as well, said frame structure being shown partly broken off in FIG. 1.

Irradiation head 9 is pivotable around two axes, namely around a vertical axis V and a horizontal axis H. Horizontal axis H extends approximately in the longitudinal direction of treatment table 1. Vertical axis V extends parallel to double arrow 5 through the head of patient 6.

The isocenter I of the radiation treatment apparatus is the common point in which horizontal axis H, vertical axis V and the axis of beam 6 meet. The adjusted target range Z' of the radiation treatment apparatus is adjusted in said isocenter as well. Beam S is generated, for example with a linear accelerator.

An irradiation or stereotaxy of the target present in the head of patient 6 can take place only if isocenter I or target range Z' is congruently positioned with target Z. Therefore, the head of the patient, which is present in stereotaxy sight unit 7, must be displaced by moving table top 2 in the direction of double arrows 3 to 5 until target Z is located exactly in isocenter I or in target range Z' of the radiation treatment apparatus.

Figure 2:
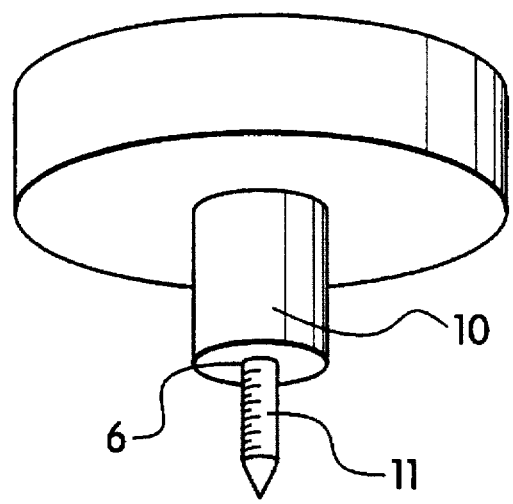
FIG. 2 is an enlarged representation of the radiation outlet zone of a radiation treatment apparatus according to FIG. 1.

FIG. 2 is a schematic and perspective view of an enlarged representation of the beam exit zone of irradiation head 9 of the radiation treatment apparatus, and in particular, radiation collimator 10. A measuring rod 11 fitted with a suitable measuring scale is inserted in the bore of the radiation outlet of radiation collimator 10 and axially displaceable in said bore. Measuring rod 11 is designed in the form of a mechanical indicator and fitted at its free end with an indicator tip.

When measuring rod 11 is pushed into or out of the radiation outlet bore of radiation collimator 10, the spacing between the face side of the radiation collimator and the tip of the indicator of measuring rod 11 can be read on the face side of radiation collimator 10 facing measuring rod 11. The point at which measuring rod 11 enters through the respective face side of radiation collimator 10 is used as a reference point b.

Figure 3:
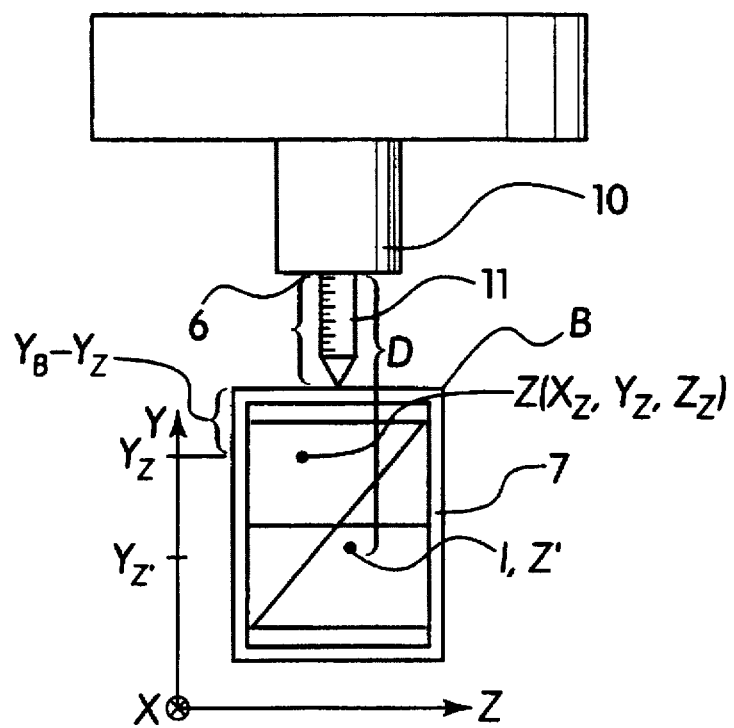
FIG. 3 is a lateral view of the radiation outlet zone according to FIG. 2, with the stereotaxy sight unit arranged underneath it.

FIG. 3 shows a lateral view of irradiation head 9. A lateral view of stereotaxy sight unit 7 is shown beneath measuring rod 11. The indicator tip of measuring rod 11 is touching the top plate of stereotaxy sight unit 7, the plate being the face-side plate with respect to the head of the patient. Therefore, the spacing between the respective collimator face side and the top plate of stereotaxy sight unit 7 can be measured with respect to reference point b. The Y-axis and the Z-axis of a reference system are indicated next to stereotaxy sight unit 7. For example, the reference system could be preset on stereotaxy sight unit 7. Target Z, such as a brain tumor in the head of patient 6, is located within stereotaxy sight unit 7. In the system of coordinates shown, target Z has the defined coordinates $X_z$, $Y_z$ and $Z_z$, which are known from a previous measurement such as computertomography.

Isocenter I or target range Z' could be initially located, for example, somewhere beneath target Z. If target Z is to be aligned with isocenter I or target range Z', table top 2 of treatment table 1 must be lowered along double arrow 5 until Z and I are disposed in the same plane, thus in a plane parallel to the reference plane B of the stereotaxy sight unit 7. If, in connection with such lowering, the stop of the indicator tip of the measuring rod 11 is retained in the reference plane B, the spacing between the reference point b and the indicator tip or reference plane B, namely the spacing d, is extended correspondingly. Target Z and isocenter I or target range Z' are located on the same level, thus in the same plane, if the spacing d plus the coordinate difference $Y_B$ minus $Y_z$ is equal to the spacing D between the reference point b and the isocenter I, said spacing D remaining constant. $Y_B$ is the Y-coordinate of the reference plane B in the system of coordinates. The position of the origin of the system of coordinates is unimportant.

FIG. 4 shows, again in a schematic and perspective view, an enlarged representation of stereotaxy sight unit 7, with indicated coordinate axes. The head of patient 6 is indicated within sight unit 7. Stereotaxy sight unit 7 is immovably fixed on the head of the patient with the help of the arms 12 and, if need be, screws, which are not shown.

Figure 4:
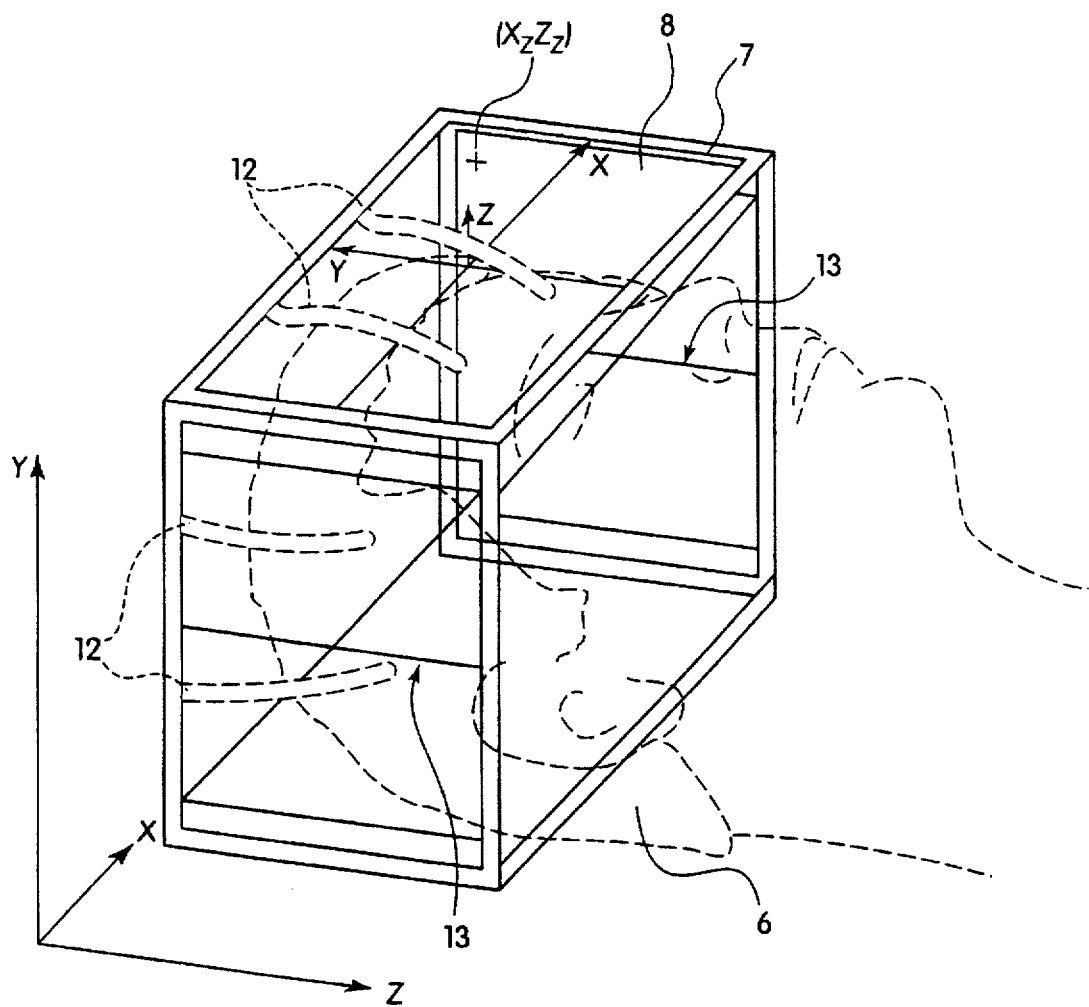
FIG. 4 is a perspective view of a stereotaxy sight unit according to FIG. 3, again with an enlarged representation.

The top, face-side plate of stereotaxy sight unit 7 corresponds with reference plane B. The two other temple-side plates of stereotaxy sight unit 7 are not required in connection with the method of the invention. However, these plates are shown in FIG. 4 in order to indicate Z-shaped markings 13 on said plates. In a computertomography, these markings may serve to fix the Z-coordinate of each computer section or sectional X-ray picture when the X-ray pictures are produced in successive planes extending parallel with the X-Y-plane. Through the Z-shape of the Z-markings 13, it is possible to recognize in the X-ray picture the bar spacings of the Z-bars, so that a Z-position of the picture plan can be read based on such spacings. However, such determination of the Z-coordinate of sectional X-ray pictures is known in the art and is part of the original determination of the coordinates of the target Z.

FIG. 4 illustrates that after the spacing d has been correctly adjusted with the help of the indicator tip of measuring rod 11, the point of intersection of the Y- and the Z-coordinates of target Z can be found by scanning reference plane B with the indicator tip. The respective coordinates $X_z$ and $Z_z$ can be marked in the reference plane B, as indicated in FIG. 4. Measuring rod 11 could also be pivoted between a resting position and an operating position.

Figure 5:
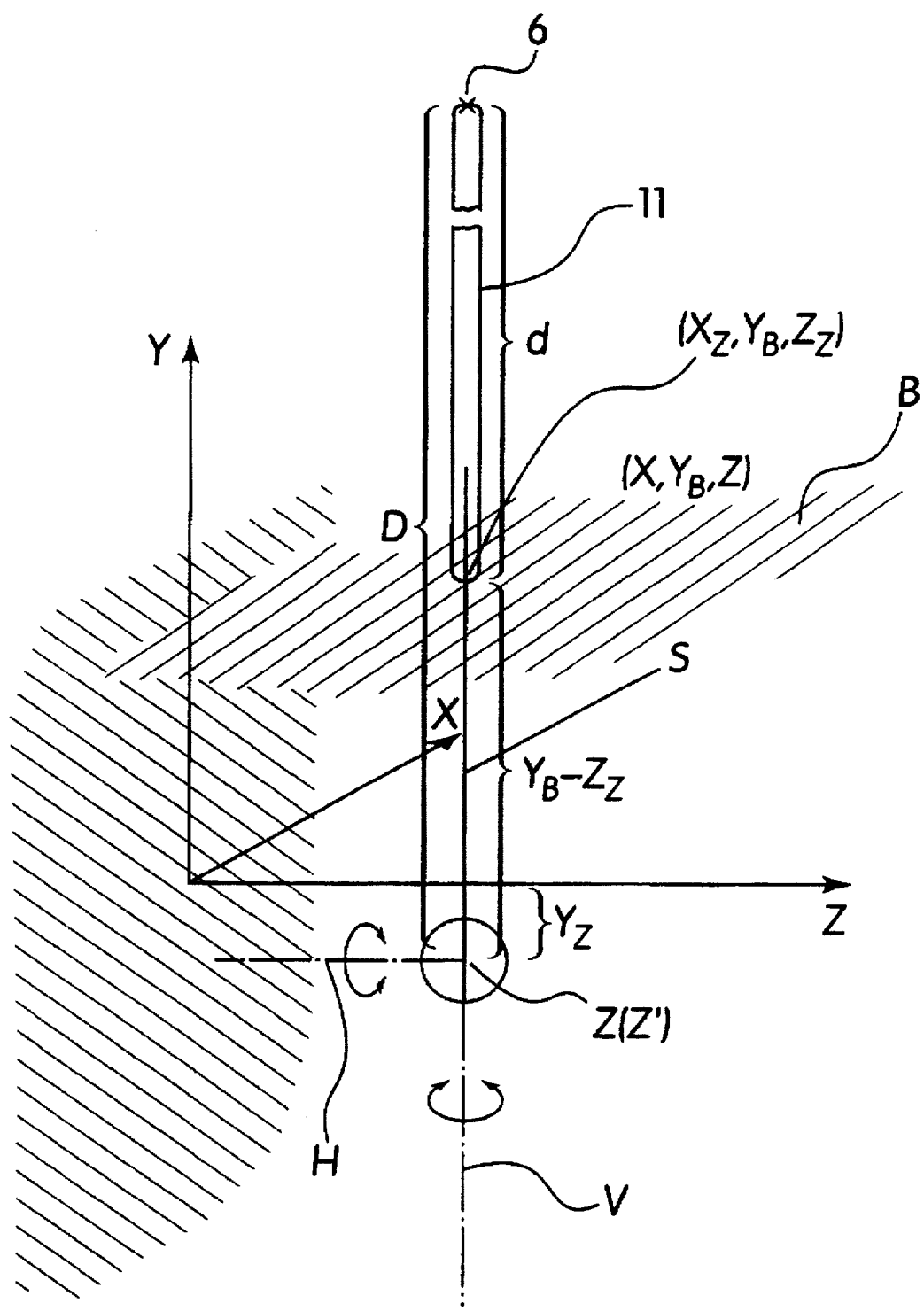
FIG. 5 is a sketch for explaining the mathematical-geometric conditions.

FIG. 5 is a perspective view of the geometric relations of FIG. 3 and FIG. 1. In a reference system predetermined by stereotaxy sight unit 7, a reference point b is selected preferably on the radiation axis of beam S. A reference plane B is selected, which is parallel with the X-Z plane of the reference system and having the coordinates (X, $Y_B$, Z). If, as shown in the reference system in FIG. 5, target Z and target range Z' have the same Y-coordinates following an alignment or positioning, spacing D between reference point b and target range Z' corresponds to the sum of spacing d between reference point b and reference plane B, plus the Y-coordinate difference $Y_B$ minus $Y_z$, and thus corresponds to the difference of the respective Y-coordinates of the target Z and the reference plane B. The difference $Y_B$ minus $Y_z$ may be directly measured by computertomography, for example on an X-ray picture. This method is particularly useful if the reference plane B is the top face-side plate of stereotaxy sight unit 7, which can be mounted on the patient's head when the patient is X-rayed, and with a Z-bar as orientation. No lateral plates are required if the Z-coordinate is determined mechanically. It is not necessary to determine the absolute Y-coordinates, because the origin of the system of coordinates is unimportant. It is also unimportant that one of the two Y-coordinates may be negative with respect to the X-Z-plane. Spacing D is measured in relation to the radiation equipment and remains constant and known. As explained in connection with FIG. 3, spacing d is adjusted as required. According to the positioning shown in FIG. 5, the X- and Z-coordinates of target Z and target range Z' correspond as well. The point of intersection of the X-coordinate with the Z-coordinate of target Z is found with the help of the indicator tip of measuring rod 11 in reference plane B in the site ($X_z$, $Y_B$, $Z_z$). The second plane shown in FIG. 5, which extends parallel with the X-Y-plane of the reference system, is not required according to the invention, but is intended only to show a clearer perspective of the perspective view.

Accordingly, while only several embodiments of the present invention have been shown and described, it is obvious that many changes and modifications may be made thereunto without departing from the spirit and scope of the invention.

What is claimed is:

1. A method for positioning a target to be irradiated with a radiation treatment apparatus, said apparatus capable of generating a beam of radiation along an axis of radiation to a target range, said target range being the exact location where the radiation beam is directed, comprising:

determining the position of the target according to coordinates on a coordinate system, said target having fixed coordinates on said system;

selecting a reference point that has a measured distance to the target range of the radiation treatment apparatus;

selecting a reference surface that has a measured distance to the target;

measuring the spacing between the reference point and the reference surface to determine one of the coordinates of the target on the reference surface;

adjusting the spacing between the reference point and the reference surface so that the target range and the target are in a same plane; and determining the other coordinates of the target on the reference surface so that the target range can be exactly aligned with the target.

2. The method according to claim 1, further comprising immovably affixing a stereotaxy sight unit to the patient, said sight unit forming the coordinate system for the coordinates of the target, said coordinate system comprising an X-axis, a Y-axis and a Z-axis, said target having an X-coordinate, a Y-coordinate and a Z-coordinate, wherein the axis of radiation is parallel to the Y-axis, wherein the reference surface is a plane extending parallel to the X-axis and Z-axis and having a fixed Y-coordinate, and wherein the spacing between the reference point and the reference surface is adjusted so that the spacing from the reference point to the target range is equal to the sum of the spacing between the reference point and the reference surface, plus the spacing between the reference surface and the target, measured along the Y-axis.

3. The method according to claim 1, wherein the spacing between the reference point and the reference surface is measured mechanically.

4. The method according to claim 1, wherein the spacing between the reference point and the reference surface is measured electronically.

5. The method according to claim 1, wherein the spacing between the reference point and the reference surface is measured optically.

6. The method according to claim 2, wherein the reference surface is a plate attached to the stereotaxy sight unit.

7. The method according to claim 6, wherein the spacing between the reference point and the reference surface is measured by placing one end of a measuring rod on the plate, so that the two coordinates of the target within the plane of the reference surface may be determined.

8. The method according to claim 1, further comprising marking on a plate the point of intersection of the coordinates of the target in the plane of the reference surface.

9. The method according to claim 1, wherein the radiation treatment apparatus is fitted with a bore from which the radiation exits, said method further comprising inserting a measuring rod into said bore for measuring the spacing between the reference point and the reference surface, said measuring rod being exactly fitted and axially movable in said bore.

10. The method according to claim 1 wherein the reference point is located on the axis of radiation.

11. A device for determining the correct position of a target to be irradiated with a radiation treatment apparatus, said apparatus comprising an irradiation head having a beam exit bore from which a beam of radiation exits along an axis of radiation to a target range, said target range being the exact location where the radiation beam is directed, and a radiation collimator mounted around said beam exit bore, said device comprising:

means for measuring the spacing between a selected reference point and a selected reference surface, said reference point having a measured distance to the target range and said reference surface having a measured distance to the target, wherein the position of said target has been determined by preset coordinates on a coordinate system, and wherein said spacing can be adjusted so that the target range and the target are in a same plane; and means for locating the coordinates of the target on the reference surface, so that the target range can be exactly aligned with the target.

12. The device according to claim 11, comprising:

a measuring rod having a first end and a second end, the first end being capable of being inserted into the beam exit bore of the radiation treatment apparatus and being axially movable within said bore; and a stereotaxy sight unit comprising a plate positioned perpendicular to the axis of radiation, wherein said plate functions as the reference surface and serves as a stop for the second end of said measuring rod.

13. The device according to claim 12, wherein the measuring rod is an indicator having a tip at the second end, and wherein said tip points at the plate when the indicator is positioned in the beam exit bore.

14. The device according to claim 13, further comprising means for marking on the plate the position of the other coordinates of the target.

15. The device according to claim 12, wherein the cross section of said measuring rod fits exactly within the beam exit bore of the radiation treatment apparatus.

16. The device according to claim 15, further comprising means attached to the radiation collimator for receiving and mounting the first end of the measuring rod.

17. The device according to claim 11, wherein said device is an independent accessory device that is mountable on the irradiation head of the radiation treatment apparatus.

18. The device according to claim 12, wherein the measuring rod is an independent accessory device that is mountable on the stereotaxy sight unit.

19. The device according to claim 11, comprising an indicator having an indicator tip, and a digitizer, wherein said indicator tip is a component of said digitizer, and wherein the reference surface functions as a digitalizing tableau.

20. The device according to claim 11, wherein said device is a contactless measuring device.

21. The device according to claim 20, wherein said device comprises a reflection and sensor device capable of emitting, reflecting and receiving an electromagnetic beam or sound wave.

* * * * *